United States Patent
Nissilä

(10) Patent No.: US 7,062,313 B2
(45) Date of Patent: Jun. 13, 2006

(54) EVALUATION OF EXERCISE STRESS LEVEL DEPENDENT PARAMETER

(75) Inventor: Seppo Nissilä, Oulu (FI)

(73) Assignee: Polar Electro Oy, Kempele (FI)

( * ) Notice: Subject to any disclaimer, the term of this patent is extended or adjusted under 35 U.S.C. 154(b) by 648 days.

(21) Appl. No.: 10/259,261

(22) Filed: Sep. 27, 2002

(65) Prior Publication Data

US 2004/0064061 A1   Apr. 1, 2004

(51) Int. Cl.
*A61B 5/04* (2006.01)

(52) U.S. Cl. ............... 600/513; 600/519; 600/520

(58) Field of Classification Search ........ 600/508–509, 600/513, 519–520, 526
See application file for complete search history.

(56) References Cited

U.S. PATENT DOCUMENTS 5,265,615 A * 11/1993 Frank et al. ............. 600/485
6,529,771 B1 * 3/2003 Kieval et al. ............ 600/509
2002/0198463 A1 * 12/2002 Dardik et al. ............ 600/520

FOREIGN PATENT DOCUMENTS

| EP | 0559203 A1 | 9/1993 |
|----|-----------|--------|
| EP | 1092453 A2 | 4/2001 |
| JP | 05212136 | 8/1993 |
| JP | 08052119 | 2/1996 |

OTHER PUBLICATIONS

U.S. Appl. No. 09/798,577, filed Mar. 2, 2001, Kinnunen et al.

* cited by examiner

*Primary Examiner*—Robert E. Pezzuto
*Assistant Examiner*—Tammie K. Heller
(74) *Attorney, Agent, or Firm*—Hoffmann & Baron, LLP

(57) ABSTRACT

A method and arrangement for estimating a stress level dependent parameter on a person that measures a person's heart rate, calculates a derivative of the measured heart rate, and estimates a value for a stress level dependent parameter by using the calculated heart rate derivative.

25 Claims, 3 Drawing Sheets

EVALUATION OF EXERCISE STRESS LEVEL DEPENDENT PARAMETER

FIELD OF THE INVENTION

The invention relates to sports, in particular to applications in which a stress level dependent parameter is evaluated in connection with a sports exercise or a competition.

BRIEF DESCRIPTION OF THE RELATED ART

Determining the stress level during an exercise is important when planning a correct relation between an athlete's energy expenditure and intensity of exercise. An exercise of excessive duration, for instance, may deplete the person's energy reserves to a disadvantageous level. Further, if the objective is to lose weight, it is important to obtain accurate information on the amount of energy consumed during an exercise.

The intensity of a workout or an exercise can be described by means of a person's heart rate. The heart rate represents the heart beat frequency in a time unit, giving heart beats per minute, for instance. Sports and exercising increase the heart muscle mass and the capability of the body to supply oxygen to muscles. The heart's capability of pumping oxygenated blood into the body improves and, consequently, by one contraction, i.e. beat, the heart is able to pump a larger amount of blood in the body. Thus, generally, the better condition a person has, the lower heart rate he/she will have with the same workload.

The person's heart rate during exercise is measured using a heart rate monitor, for instance. A heart rate monitor is a device that measures heart rate, for instance, on the chest from an electric signal transmitted by the heart and displays the measured heart rate on its display. Heart rate monitors often comprise a plurality of other facilities apart from the heart rate measurement, such as assessment of energy consumption during exercise. U.S. patent application Ser. No. 09/798,577 shows one prior art solution for assessing the energy consumption of a person during an exercise.

Current solutions for evaluating the value of an exercise stress level related parameter, such as energy consumption, do not take into account the variation direction and/or speed of the heart rate. Current linear or piecewise linear models thus provide inaccurate results for the energy consumption, or a corresponding parameter.

SUMMARY OF THE INVENTION

An object of the invention is to provide an improved method and equipment for assessing the value of an exercise stress level dependent parameter. This is achieved by a method for estimating a value for an exercise stress level dependent parameter in a training session performed by a person, comprising measuring the person's heart rate, calculating a derivative of the measured heart rate, and estimating the value for an exercise stress level dependent parameter using the calculated heart rate derivative.

The invention also relates to an arrangement for estimating an exercise stress level dependent parameter on a person, comprising means for measuring the person's heart rate, means for calculating a derivative of the measured heart rate and means for estimating the value for an exercise stress level dependent parameter by using the calculated heart rate derivative.

Embodiments of the invention are disclosed in the dependent claims.

The invention thus relates to a method and an arrangement for evaluating the value of an exercise stress related parameter in an exercise or a sports training session. In the description of the invention, the exercise refers to a physical exercise that is performed at a higher heart rate level than the resting heart rate. Broadly speaking, the invention relates to assessing human energy consumption when the heart rate level exceeds 80 beats per minute. The exercise stress level dependent parameter is, for instance, the energy consumption of the person. The energy consumption in an exercise in characterized by a quantity such as "calories (Cal)/time unit" or "calories/exercise". The exercise stress level dependent parameter can also be an endurance parameter obtained, for instance, by using cumulative heart-rate information.

In the invention the heart rate of a person is measured during an exercise. From the measured heart rate information, a derivative of the heart rate is calculated. The derivative of the heart rate gives information about whether the heart rate is increasing or decreasing. The derivative also gives information on the increasing/decreasing speed of the heart rate. The calculation of the derivative can be, for instance, averaged over a period of one minute or five minutes of measured heart rate information. In the invention, the knowledge of the derivative is utilized in the estimation of a value for the exercise stress related parameter.

In an embodiment, two dependencies between the exercise stress level and an exercise stress level dependent parameter are utilized in the estimation of the value for the exercise stress level dependent parameter. A first dependency is utilized when the derivative of the heart rate indicating the exercise stress level is positive and a second dependency is utilized when the heart rate derivative is negative. A different model for estimating the value of the exercise stress level dependent parameter is then used when the heart rate is increasing compared to a situation when the heart rate is decreasing. In a practical application, this could mean that the first dependency and the second dependency form a hysteresis dependency, where the two dependencies form parabolas extending to both sides of a basic dependency, which can be a linear dependency model. Practically, when the heart rate is increasing, the energy consumption is higher than a linear relationship suggests, and when the heart rate is decreasing, the real energy consumption is less than a linear model suggests.

In an embodiment, the first dependency and/or the second dependency is/are adjusted in a personalization phase according to one or more physiological parameters of the person. A physiological parameter can be for instance weight, sex, age or a corresponding parameter describing the physiology of the person.

In an embodiment, the first dependency and/or the second dependency is/are adjusted according to the condition of the person. Taking the effect of the condition into consideration, it is possible to recognize the fact that at a given heart rate level, a fit person consumes more energy than an unfit person. Taking the condition into account, it is also possible to utilize the fact that the derivative of the heart rate in relation to the energy consumption follows more closely to the linear relationship for a fit person than that for an unfit person. The condition can be determined in the personalization phase, which can be performed prior to the exercise or later on. The condition can be determined by using the user parameters or it can be determined in a reference exercise. The condition assessment obtained is utilized in a similar manner to physiological parameters in assessing the energy consumption on the basis of the heart rate information during the exercise. The physical condition mentioned can be described, for instance, by the maximal oxygen uptake value, the maximum value of running or swimming speed or by the maximum performance when pedaling an exercise bike.

In an embodiment, the first dependency and/or the second dependency is/are adjusted during exercise depending on the magnitude of the derivative. Then, if the derivative is large, the hysteresis effect in the first dependency and the second dependency is greater. In another embodiment, several dependency functions are formed in the personalization phase, and one of them is chosen according to the actual magnitude/direction of the heart rate derivative. The one or more hysteresis dependencies can be created by using a neural network approach, for instance.

An example of an arrangement for implementing the invention is the heart rate monitor. The apparatus implementing the invention can, for instance, be a heart rate monitor. A heart rate monitor is a device employed in sports to measure human heart rate information either from an electrical impulse transmitted by the heart or from the pressure produced by the heart beat on an artery, or optically from blood flow in a blood vessel. Heart rate monitors have a variety of different structures. A heart rate monitor can be a two-piece device comprising an electrode belt to be fitted around the user's chest to measure the heart rate by means of two or more electrodes. The electrode belt transmits the measured heart rate information inductively to a wrist-worn receiver unit. On the basis of the received magnetic pulses, the receiver unit calculates the heart rate and other heart rate variables, such as the moving average of the heart rate. In the present invention, variables, such as an exercise stress level of the user, the cumulative consumed energy or the consumed energy per time unit, are formed in the heart rate monitor.

The invention provides a significant advantage over the prior art. The advantage is that by using the method and arrangement according to the invention, the calculation of a stress dependent parameter can be made more precise.

BRIEF DESCRIPTION OF THE DRAWINGS

In the following, the invention will be described in greater detail and with reference to the attached drawings, in which.

DETAILED DESCRIPTION OF THE PREFERRED EMBODIMENTS

Figure 1A:
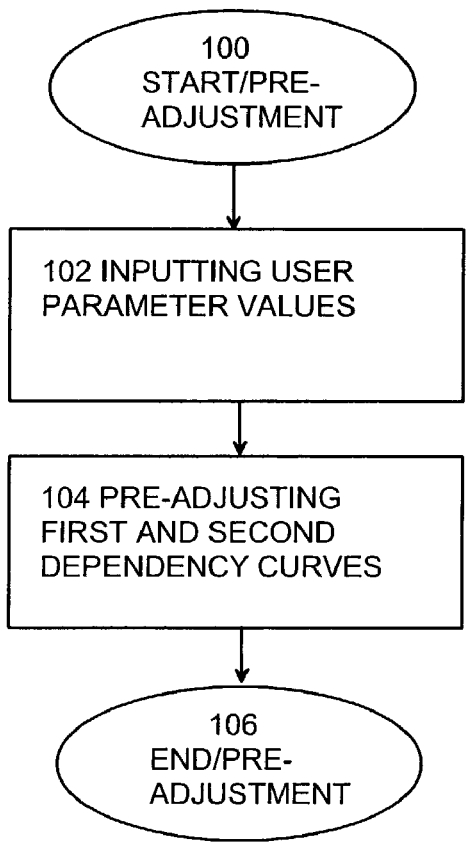
FIG. 1A shows an embodiment of a pre-adjustment phase in the method according to the invention.
Figure 1B:
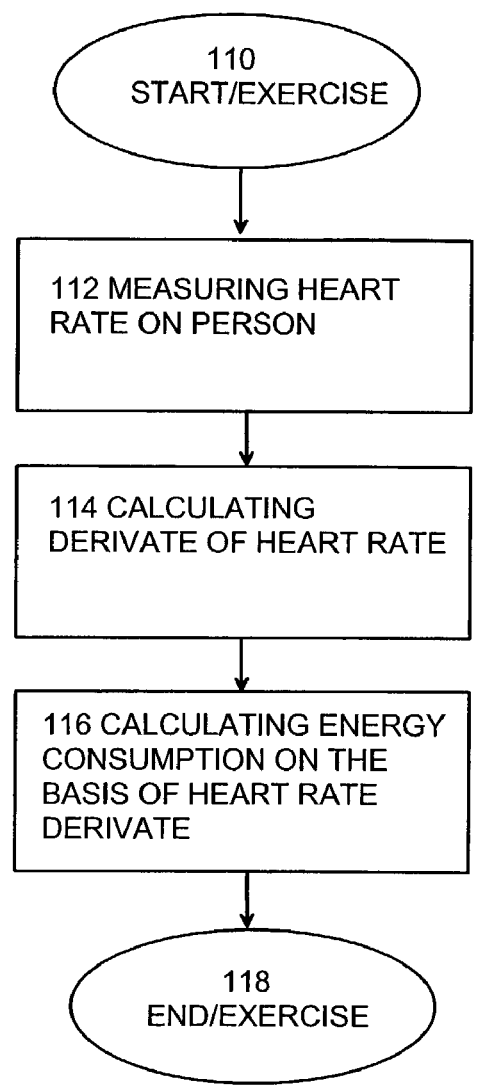
FIG. 1B shows an embodiment of an exercise phase in the method according to the invention.

In the following, the invention will be described with reference to embodiments shown in the attached drawings. FIGS. 1A and 1B show an example of a method according to the invention. FIG. 1A describes a personalization phase, which can be performed prior to an exercise. FIG. 1B describes a usage phase functions performed during an exercise.

The purpose of the personalization phase is to set the equipment implementing the method to give the best possible results for the assessment of an exercise stress level dependent parameter in the usage phase. In the personalization phase, user parameters are requested from a user, as described in step 102. In a heart-rate monitor, the user parameters can be inputted using, for instance, the keyboard or user buttons of a heart rate monitor. The user parameters asked from the user can be user parameters describing the user's physiology, such as the age, sex and weight. The user parameters can also be parameters describing the condition of the user, such as the sporting activity level of the person or the maximum oxygen uptake. The personalization phase can also contain determination of a user's condition in a reference exercise.

Method step 104 describes the adjustment of a first and a second dependency curve describing the relationship between the exercise stress level and the stress level dependent parameter for the user. The values of user parameters can be taken into account by using, for instance, a neural network model. In the neural network model, information is gathered on hundreds or even thousands of users in order to find a weighting scheme for different user parameters. The weighting scheme is stored in a heart rate monitor as data and as rules between parameters. When the neural network model is utilized for a new user, the user parameters are inputted to the model. The neural network model then finds the most suitable output parameters to the given input parameters by using its information and knowledge base. When applied to the current example of the invention, the neural network model gives as an output the dependency between the exercise stress level and an exercise stress level dependent parameter. The exercise stress level parameter can, for instance, be the heart rate, and the dependent parameter can be the energy consumption of the person. The exercise stress level parameter can also be the variance of the heart rate, for instance. The exercise stress level dependent parameter can also be the endurance level of the person, for instance.

Figure 2:
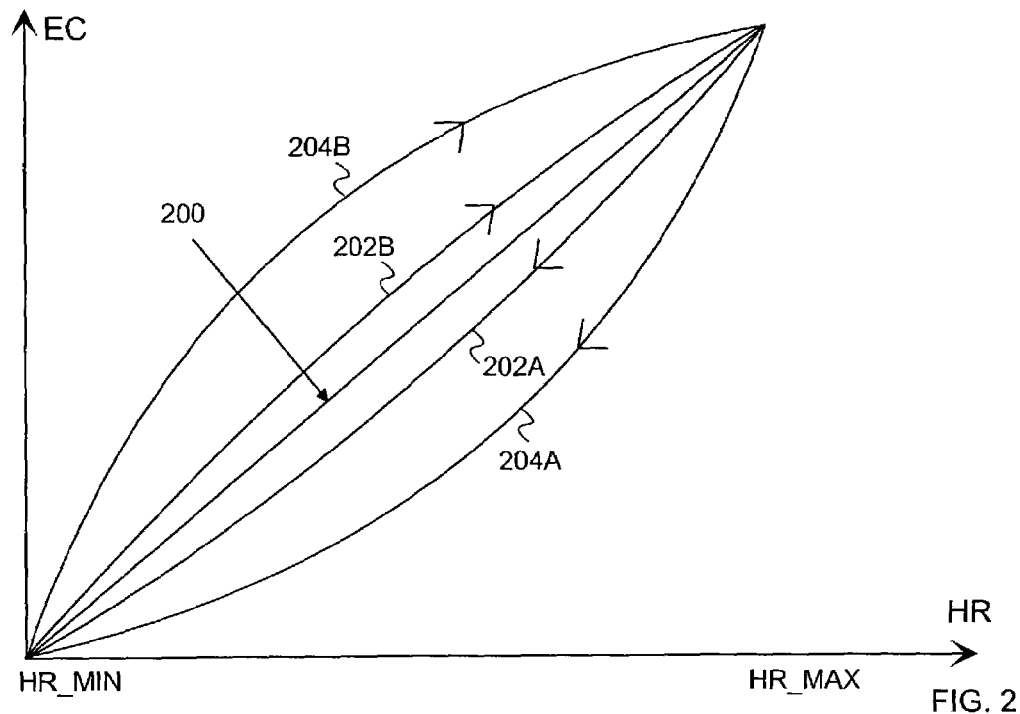
FIG. 2 shows energy consumption dependency curves for a fit and an unfit person.

FIG. 2 shows two examples of the relationships between an exercise stress level and a stress level dependent parameter, which relationships are obtained as a result from the personalization phase described in FIG. 1A. The exercise stress level on the x-axis is illustrated by the heart rate of a user. The exercise stress level dependent parameter on the y-axis in FIG. 2 is the energy consumption of the person. FIG. 2 shows a linear basic relationship 200 between the heart rate and the energy consumption. The relationship 200 need not necessarily be a fully linear relationship but can instead be a piecewise linear relationship or some other known relationship. Functions 202A and 202B illustrate the energy consumption of a fit person and functions 204A and 204B illustrate the energy consumption in the function of the heart rate for an unfit person. The arrows in the functions 202A to 204B indicate the direction of the heart rate derivative, that is, the curve 202A is utilized for calculating the energy consumption for a fit person when his/her heart rate is decreasing. Correspondingly, the function 202B is used for a fit person when his heart rate is increasing or the heart rate derivative is positive. The functions 202A and 202B, for instance, show that the estimation of the energy consumption provides higher values for energy consumption when the heart-rate derivative is positive than when the derivative is negative.

For an unfit person, the first dependency 204B indicates an increasing heart rate and the second dependency 204A indicates calculating energy consumption when the heart rate is decreasing. In FIG. 2, it can be seen that the energy consumption has greater variation with respect to the basic variation in the case of an unfit person when compared to a fit person.

FIG. 1B shows an example of the method when applied to an exercise performance. During the exercise, the heart rate is measured as shown in step 112, on the person performing the exercise. The exercise can be herein defined as an athletic performance, an athletic competition or the like, where the heart rate level rises higher than the resting level. The heart rate level is then typically between 80 beats per minute and the maximum heart rate. The heart rate can be measured using a heart rate monitor used in sports. In step 114, a derivative of the heart rate is calculated. The calculation of the derivative is illustrated by the following table.

TABLE 1

Heart rate of a person during an exercise

| Time | Heart rate | Sign | Magnitude |
|---|---|---|---|
| 0:00 | 70 | | |
| 1:00 | 73 | + | 3 |
| 2:00 | 77 | + | 4 |
| 3:00 | 78 | + | 1 |
| 4:00 | 82 | + | 4 |
| 5:00 | 84 | + | 3 |
| 6:00 | 87 | + | 3 |
| 7:00 | 90 | + | 2 |
| 8:00 | 92 | + | 3 |
| 9:00 | 95 | + | 3 |
| 10:00 | 97 | + | 2 |
| 11:00 | 93 | − | 4 |
| 12:00 | 92 | − | 1 |
| 13:00 | 90 | − | 1 |
| 14:00 | 88 | − | 1 |
| 15:00 | 85 | − | 2 |

Table 1 shows that the exercise begins at a heart rate level of 70 beats per minute. After one minute, the heart rate has come up to a level of 73 beats per minute. Alternatively, the value given at the time instant of one minute is the average heart rate within the first minute of the exercise. A heart rate monitor can give the heart rate each second, so the value after the first minute is the average of 60 measurement results of the heart rate. Table 1 shows that during the exercise, the heart rate increases for the first 10 minutes, whereafter the heart rate starts declining. That is, during the first 10 minutes the derivative of the heart rate is positive, and between 11–15 minutes the derivative is negative. The rightmost column in Table 1 shows the magnitude of the change in the derivative.

In step 116 of FIG. 1B, the energy consumption is estimated on the basis of the heart rate derivative. This is further illustrated in FIG. 3, which shows few calculation functions 300A to 302C for a person. Functions 300A to 300C show examples of the first dependency when the heart rate derivative is positive and functions 302A to 302C show the second dependency when the heart rate derivative is negative. The greater the magnitude of the derivative is, the further away the dependency is chosen as seen from the basic relationship 200. For instance, if the magnitude of the derivative is +1, the momentary energy consumption value is calculated from the function 300A, and if the magnitude of the derivative is −2, the momentary energy consumption value is chosen from a curve 302B. So, during the exercise, the calculation of the energy consumption can be based on discrete measurement results, where the discrete energy consumption values are chosen from different functions 300A to 302C.

Figure 3:
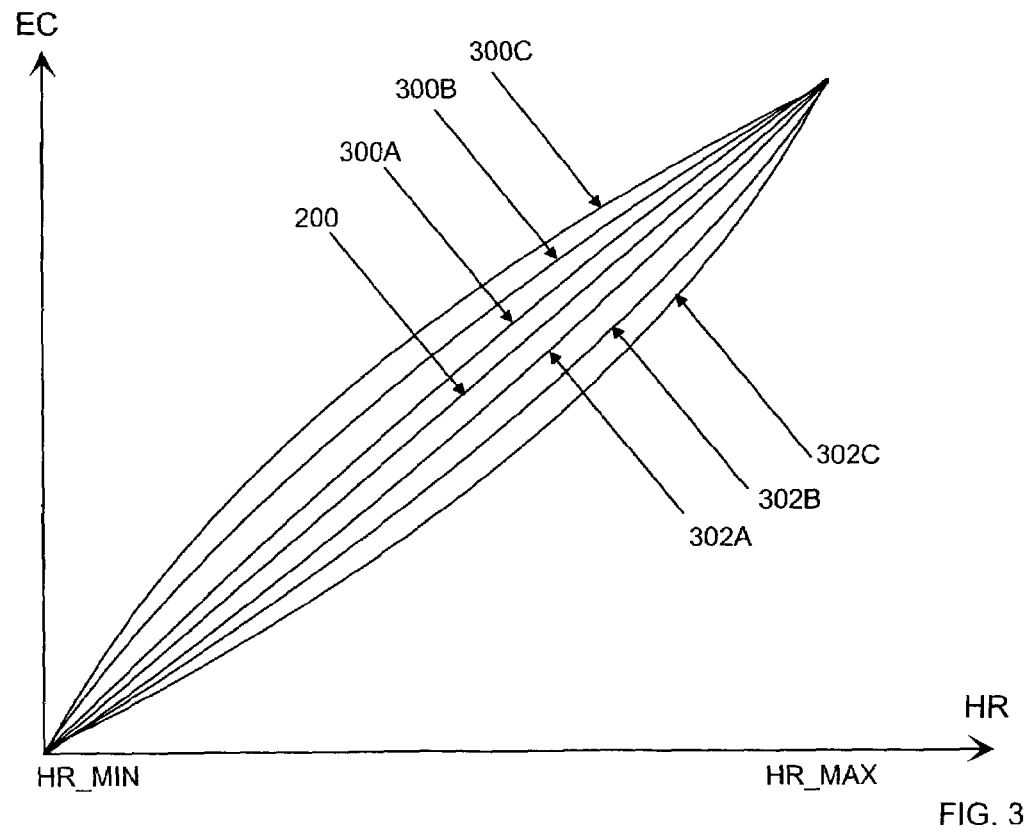
FIG. 3 shows energy consumption functions for a person, the functions illustrating various derivatives of the heart rate.

In addition to the solution shown in FIG. 3, the dependency between the magnitude of the derivative and the heart rate can also be based on one relationship formed in the personalization phase. This relationship is then adjusted depending on the magnitude of the derivative. The adjustment can be performed for instance by multiplying or summing a certain parameter into the calculation model, such as the model given in FIG. 2. For example, if the basic function formed for a user is 202A to 202B, this function can be adjusted by applying a parameter to the function to give dependencies shown in FIG. 3. Although FIG. 3 only shows a few curves for the calculation of energy consumption or a similar parameter, there can practically be much more of such calculation functions. In other words, if the calculation parameter value is at a first time instance chosen from the curve 302C, the value at the next moment can be chosen from a curve not shown in between the curves 302B and 302C. The resolution of the calculation can thus be much more precise than shown in FIG. 3.

Figure 4:
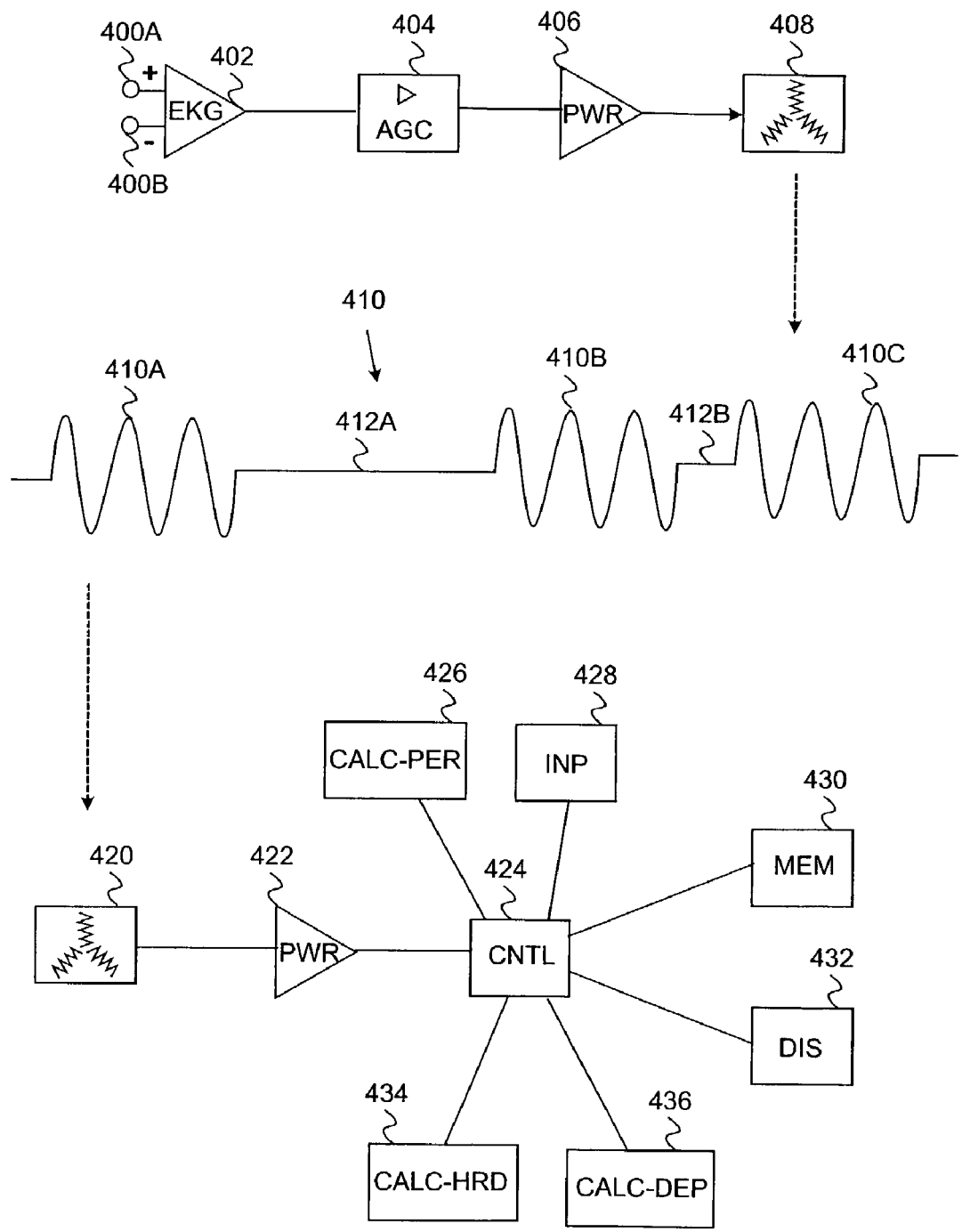
FIG. 4 shows an embodiment of an arrangement according to the invention.

FIG. 4 shows an embodiment of the equipment according to the invention. A heart rate monitor shown in FIG. 4 contains an electrode belt to be placed onto a person's chest. The electrode belt contains components 400A to 408. The heart rate monitor also contains a receiver unit having components 420 to 436. In the personalization phase, user parameters are converted into two or more functions describing the dependency between the heart rate and a heart rate dependent parameter. In the personalization phase, the user thus inputs user parameters using the input means 428, which can be a keypad, a microphone for a speech or a voice controller, or a telecommunication port for entering data from external equipment, such as a personal computer. The heart monitor also contains a presenting means 432 for presenting the heart rate or the heart rate variables derived from the heart rate, such as the energy consumption. By the presenting means 432 it is also possible to display instructions for the person using the heart rate monitor, for instance, in giving the user parameters. The presenting means 432 is, for instance, a display, a speech controller or a means for transmitting the heart rate and/or feedback information to an external computer or data network for presenting them separately from the heart rate monitor. Also relating to the personalization phase, the heart rate monitor also comprises personalization means 426 for personalizing the calculation of the stress dependent parameter. Personalization means, for instance, receives user parameters as input and forms different dependency curves for the user to be used in the calculation of the stress dependent parameter.

The heart rate of a person performing an exercise is measured by means of a transmitter electrode belt. The transmitter electrode belt measures heart rate information by measuring means. The measuring means are, for instance, two or more electrodes 400A and 400B. From the electrodes, the heart rate signal is applied to an ECG preamplifier 402, wherefrom the signal is transferred via an AGC amplifier 404 and a power amplifier 406 to a transmitter 408. The transmitter 408 can be implemented as a coil, which sends the heart rate information 410 inductively to a receiver. One 5 kHz burst 410A corresponds to one heart beat, for instance, or a plurality of bursts 410A to 410C may correspond to one heart beat. The intervals 412A to 412B of bursts 410A to 410C can be equal in length or mutually different in length. Instead of inductive transmission, the information between the electrode belt and the receiver unit can be transmitted optically or via a conductor, for instance.

In an embodiment, the receiver unit 420 to 436, such as a wrist-worn receiver, comprises a receiver coil 420, from which the received signal is applied through a signal receiver 422 to a central processor 424, which coordinates the operation of the different parts of the receiver unit. The receiver unit can also comprise a memory 430 for storing the heart rate information and/or energy consumption information. For instance, if an average heart rate needs to be calculated, heart rate information on one-minute time could be stored in the memory. The receiver unit further comprises means 426 for personalizing, which can calculate energy consumption curves shown in FIG. 3 for a user. In this calculation, the heart rate monitor can use user information, such as information on physiological properties of the person and/or the condition of the person. The receiver unit also comprises calculation means 434 for calculating a heart rate derivative and calculation means 436 for calculating a value of the heart rate dependent parameter on the basis of the heart rate and the heart rate derivative. It is obvious to a person skilled in the art that the heart rate monitor may also comprise other parts than those shown in FIG. 4, but it is not relevant to describe them herein.

The invention can be implemented, for instance, by means of software on a general-purpose processor, as ASIC, by separate logic components or in any corresponding, known manner.

Even though the invention has been described above with reference to the examples of the attached drawings, it is obvious that the invention is not restricted thereto but it can be modified in a variety of ways within the scope of the inventive idea of the attached claims.

The invention claimed is:

1. A method for estimating a value for an exercise stress level dependent parameter in a training session performed by a person, comprising:
   measuring the person's heart rate;
   calculating a derivative of the measured heart rate; and
   estimating the value for an exercise stress level dependent parameter using the calculated heart rate derivative, wherein when estimating the value of the exercise stress level dependent parameter, a first dependency between the exercise stress level dependent parameter and the heart rate is used when the derivative is positive, and a second dependency between the exercise stress level dependent parameter and the heart rate is used when the derivative is negative.

2. The method of claim 1, wherein the exercise stress level dependent parameter is the energy consumption of the person.

3. The method of claim 1, wherein the first dependency and the second dependency form a hysteresis dependency, where the first dependency provides higher values for the exercise stress level dependent parameter than does the second dependency.

4. The method of claim 1, wherein the first dependency contains a group of dependencies, and the dependency is selected on the basis of the magnitude of the derivative.

5. The method of claim 1 wherein the second dependency contains a group of dependencies, and the dependency is selected on the basis of the magnitude of the derivative.

6. The method of claim 1, wherein the value given by the first dependency and/or the second dependency depends on the magnitude of the derivative.

7. The method of claim 1 wherein the value given by first dependency and/or the second dependency depends on the physical condition of the person.

8. The method of claim 7, wherein the physical condition is characterized by one or more of the following parameters: oxygen uptake, speed, performance in a reference exercise.

9. The method of claim 1, further comprising:
   adjusting the first dependency and/or the second dependency depending on one or more physiological parameters of the person.

10. The method of claim 7, wherein the physiological parameter is age, gender, weight or height.

11. The method of claim 1, wherein the first dependency and/or the second dependency is formed using a neural network.

12. The method of claim 1 wherein the heart rate information is measured using a heart rate monitor during exercise, and the value for the exercise stress level dependant parameter is estimated in the heart rate monitor, and the estimated energy consumption assessment is displayed on the display of the heart rate monitor.

13. An arrangement for estimating an exercise stress level dependent parameter on a person, comprising:
   means for measuring the person's heart rate;
   means for calculating a derivative of the measured heart rate; and
   means for estimating the value for an exercise stress level dependent parameter by using the calculated heart rate derivative, wherein the estimating means is configured to use a first dependency between the exercise stress level dependent parameter and the heart rate when the derivative is positive, and to use a second dependency between the exercise stress level dependent parameter and the heart rate when the derivative is negative.

14. The arrangement of claim 13, wherein the exercise stress level dependent parameter is the energy consumption of the person.

15. The arrangement of claim 13, wherein the first dependency and the second dependency form a hysteresis dependency, where the first dependency provides higher values for the exercise stress-level dependent parameter than does the second dependency.

16. The arrangement of claim 13, wherein the first dependency contains a group of dependencies, and the estimating means is configured to select a dependency on the basis of the magnitude of the derivative.

17. The arrangement of claim 13, wherein the second dependency contains a group of dependencies, and the estimating means is configured to select a dependency on the basis of the magnitude of the derivative.

18. The arrangement of claim 13, wherein the estimating means is configured to adjust the first dependency and/or the second dependency depending on the magnitude of the derivative.

19. The arrangement of claim 13, wherein the estimating means is configured to adjust the first dependency and/or the second dependency depending on the physical condition of the person.

20. The arrangement of claim 19, wherein the physical condition is characterized by one or more of the following parameters: oxygen uptake, speed, performance in a reference exercise.

21. The arrangement of claim 13, wherein the estimating means is configured to adjust the first dependency and/or the second dependency depending on one or more physiological parameters of the person.

22. The arrangement of claim 21, wherein the physiological parameter is age, gender, weight or height.

23. The arrangement of claim 13, wherein the first dependency and/or the second dependency is formed using a neural network.

24. The arrangement of claim 13, wherein the arrangement comprises means for presenting the estimated value for the heart rate dependent parameter.

25. The arrangement of claim 13, wherein the arrangement is a two-piece heart rate monitor comprising a transmitter unit and a receiver unit.

* * * * *